United States Patent
Pickell et al.

(10) Patent No.: US 10,180,062 B2
(45) Date of Patent: Jan. 15, 2019

(54) GAS EXTRACTION CALIBRATION SYSTEM AND METHODS

(71) Applicant: Weatherford Technology Holdings, LLC, Houston, TX (US)

(72) Inventors: Mark D. Pickell, Kingwood, TX (US); Doug Law, Devon (GB); Aurel Brumboiu, Calgary (CA); Wilfred Ovedhe, Calgary (CA)

(73) Assignee: Weatherford Technology Holdings, LLC, Houston, TX (US)

( * ) Notice: Subject to any disclaimer, the term of this patent is extended or adjusted under 35 U.S.C. 154(b) by 137 days.

(21) Appl. No.: 15/076,505

(22) Filed: Mar. 21, 2016

(65) Prior Publication Data

US 2017/0268333 A1    Sep. 21, 2017

(51) Int. Cl.
| | |
|---|---|
| *E21B 49/00* | (2006.01) |
| *E21B 21/06* | (2006.01) |
| *G01N 1/22* | (2006.01) |
| *G01N 33/28* | (2006.01) |

(52) U.S. Cl.
CPC .......... *E21B 49/005* (2013.01); *E21B 21/067* (2013.01); *G01N 1/22* (2013.01); *G01N 33/2823* (2013.01); *G01N 2001/2229* (2013.01)

(58) Field of Classification Search
CPC . E21B 21/067; E21B 40/005; G01M 33/2823
See application file for complete search history.

(56) References Cited

U.S. PATENT DOCUMENTS

| | | |
|---|---|---|
| 2,745,282 A | 3/1953 | Rochon |
| 4,565,086 A | 1/1986 | Orr, Jr. |
| 4,635,735 A * | 1/1987 | Crownover ........... E21B 21/067 175/42 |
| 4,765,182 A | 8/1988 | Boone |
| (Continued) | | |

FOREIGN PATENT DOCUMENTS

EP    2703597 A1    3/2014

OTHER PUBLICATIONS

Brumboiu, A.O. et al.; "Application of Semipermeable Membrane Technology in the Measurement of Hydrocarbon Gases in Drilling Fluids"; Society of Petroleum Engineers; 2000; pp. 1-15.

(Continued)

*Primary Examiner* — John Fitzgerald
(74) *Attorney, Agent, or Firm* — Blank Rome LLP

(57) ABSTRACT

A system and method calibrate efficiency of a gas extraction system in extracting hydrocarbons from mud flowing in a drilling operation. A background reading of a hydrocarbon is extracted from the mud flowing in the drilling operation with the gas extraction system and is checked for stability. An injection operation injects a known concentration of the hydrocarbon into mud, and a subject reading of the hydrocarbon is obtained with the gas extraction system during the injection operation. A correction factor of the hydrocarbon is determined for the gas extraction system by comparing the subject reading against its corresponding known concentration. Then, at least one operational reading of the hydrocarbon extracted from the mud with the gas extraction system can be corrected using the determined correction factor.

21 Claims, 5 Drawing Sheets

(56) References Cited

U.S. PATENT DOCUMENTS

| | | | |
|---|---|---|---|
| 4,833,915 A * | 5/1989 | Radd | E21B 49/005 73/152.04 |
| 4,904,603 A * | 2/1990 | Jones | E21B 49/005 175/42 |
| 5,199,509 A | 4/1993 | Wright et al. | |
| 5,277,263 A | 1/1994 | Amen | |
| 5,447,052 A | 9/1995 | Delaune et al. | |
| 5,648,603 A | 7/1997 | Hanson | |
| 6,974,705 B1 | 12/2005 | Brumboiu et al. | |
| 7,111,503 B2 | 9/2006 | Brumboiu et al. | |
| 7,392,138 B2 | 6/2008 | Frechin et al. | |
| 7,658,094 B2 | 2/2010 | Brumboiu et al. | |
| 7,844,400 B1 | 11/2010 | Selman et al. | |
| 8,011,238 B2 | 9/2011 | Hanson | |
| 2004/0065440 A1 | 4/2004 | Farabee et al. | |
| 2006/0224333 A1 | 10/2006 | Frechin et al. | |
| 2007/0043248 A1 | 2/2007 | Wu et al. | |
| 2010/0089120 A1 | 4/2010 | Hanson | |
| 2010/0139386 A1 | 6/2010 | Taylor | |
| 2010/0198533 A1 | 8/2010 | Peacock et al. | |
| 2011/0000294 A1 | 1/2011 | Kimour et al. | |
| 2011/0061439 A1 * | 3/2011 | Dong | E21B 49/08 73/1.03 |
| 2011/0094736 A1 | 4/2011 | Evrard | |
| 2011/0303463 A1 | 12/2011 | Lessi | |
| 2012/0234599 A1 | 9/2012 | Brumboiu | |
| 2014/0067307 A1 * | 3/2014 | Guerriero | G01N 33/2823 702/100 |
| 2016/0010453 A1 * | 1/2016 | Breviere | G01N 30/88 175/40 |
| 2017/0226852 A1 * | 8/2017 | Fornasier | E21B 49/08 |

OTHER PUBLICATIONS

Wright, Alan C. et al.; "A New Quantative Technique for Surface Gas Measurements"; Society of Petrophysicists and Well-Log Analysts; 1993; pp. 1-29.

Weatherford International, Ltd.; "Weatherford Surface Logging Systems—Introducing the New GC-Tracer"; http://www.inter-log.com/pros_gctracer_html; Feb. 3, 2011; pp. 1-2.

Roberts, G.L. et al.; "New System Provides Continuous Quantitative Analysis of Gas Concentration in the Mud During Drilling"; SPE Drilling Engineering; Sep. 1991; pp. 219-224 & pp. 7-10 (figures).

Int'l Search Report and Written Opinion in counterpart PCT Appl. PCT/US2017/022681, dated Jul. 7, 2017, 11-pgs.

* cited by examiner

GAS EXTRACTION CALIBRATION SYSTEM AND METHODS

BACKGROUND OF THE DISCLOSURE

In the mud logging field, one of the parameters of interest is the amount (i.e., concentration) of gas in the mud returning from the drilled well. There are different methods used to extract the gases from the mud. For example, mechanical agitators can be used in Gas Traps (included Constant Volume and Heated ones) to extract gas, or semipermeable membranes and other devices can be used. The extracted gases are then mixed with a carrier or transport gas (usually air or other convenient gas) and sent to analytical measurement device(s) that measures the gas concentration in the mixture with the carrier.

As one example, FIG. 1 shows a drilling system 10 that uses a gas trap (or degasser) and gas detection equipment to detect gasses in drilling mud leaving the flow line 16 from the wellbore. The drilling system 10 has a possum belly 20, a gas trap 50, a shaker 25, a mud pit 30, pumps 40, and other common components. In a typical installation, the gas trap 50 is fixed in the possum belly 20 from the flow line 16 at a fixed immersion level. As is known, the possum belly 20 is a container positioned at the head of the shale shaker 25 and is used to slow the drilling mud coming from the flow line 16 before passing over the shale shakers 25.

One example of a gas trap for use with such a drilling system is a Quantitative Gas Measurement (QGM) gas trap developed by Texaco and the Gas Research Institute in the 1990's. As background, the gas trap 50 shown in FIG. 2 can be similar to the device disclosed in U.S. Pat. No. 5,199,509. The trap 50 works as a centrifugal pump. A chamber 52 of the gas trap 50 is immersed in the drilling mud to an immersion level I. As a motor 60 spins an agitator 62 in the chamber 52, drilling mud is drawn up into the trap from a bottom inlet 54 and exits through a side pipe 55 immersed in the drilling mud. Air flow is brought in and out of the top of the trap 50 from a vent line 56 to a sample line 58. A pneumatic line links the gas trap's sample line 58 to the detection equipment (18), such as a chromatograph, IR total gas detector, or the like. Inside the chamber 52, a ring and baffle arrangement 64 can stabilize the mud circulation and increase the amount of time that the mud resides in the trap's container 52.

Historically, the first mud logging gas quantification procedures were done by comparison with a secondary extraction system (the so called steam or microwave still). An example of these procedures are detailed in QGM Quantitative Gas Measurement System by Texaco Inc. and Gas Research Institute (Chicago Ill.), Users Guide.

The above technology is used in connection with U.S. Pat. No. 5,199,509 that describes an improved Gas Trap, and with U.S. Pat. No. 5,447,052 that describes the Microwave Extraction of gases. Also, U.S. Pat. No. 8,011,238 describes quantification that uses Steam or Microwave still or comparison to PVT data.

One approach to quantify a gas extraction system uses a Constant Volume Trap (CVT). A constant flow of mud is sampled usually through a pump and sent to the gas extraction device (Gas Trap). After the pump, there may be a heater installed to raise the mud temperature to some higher values to improve the gas extraction. In this case, such a system is known as Heated Constant Volume Trap (HCVT).

For such systems, the quantification of the gas in mud is done on a certain volume of mud previously sampled in a separate container and then passed through the extraction system (CVT or HCVT) and collected in another container. Then, the mud collected is passed again through the extraction system and so on for a few cycle times. Mathematical functions are determined from the gas readings during the successive passes and are then used to quantify the original gas in mud amount. This kind of approach is described in U.S. Pat. No. 7,392,138, US 2011/0303463, and US 2014/0067307. The absolute gas in mud amount is an inferred value based on mathematical calculations and may be affected by the accuracy of the experimental, successive extraction runs.

Another approach can be used for gas extractions systems having a semipermeable membrane. In this approach, the semipermeable membrane is able to extract gases from the liquid mud based on the partial pressure difference of a gas outside the membrane (gas in mud) and inside the membrane. A carrier flow inside the membrane continuously swipes permeated gas and sends it to the analytics. In the meantime, the device keeps its partial pressure at low values to favor the permeation of gases from outside. The membrane is permeable only to gas and impermeable to liquid so this allows the device to be installed in a closed loop where a known amount of mud is circulated.

In a closed loop, amounts of gas of interest are injected. Then, the gas sampled through the membrane can be quantified to a true amount of gas in mud because of the known volumes of gas that were injected in a known mud volume. Such a volumetric injection quantification approach for semipermeable membranes is briefly described in SPE 62525 (June 2000). Yet, determining quantifications of each and every mud type in real-world implementations is difficult and time-consuming.

Finally, U.S. Pat. No. 5,648,603 discloses a way to quantitatively measure and detect gas entrapped in drilling fluid by injecting a known quantity of a standard gas into the evolved gas stream.

One problem with the various prior art approaches centers around the ability to translate the measured concentrations to actual concentrations of gas in mud because different gas types (different hydrocarbons) are extracted from the mud at a different rate due primarily to the different solubility of the gases in the mud. This is known in the technical literature as Trap Efficiency or Trap Factors or Solubility Correction Coefficients, Trap Calibration, or other names.

Determining the efficiency of gas extraction using conventional tools such as Gas Traps, Constant Volume Trap devices (including Heated), and others can be problematic. In fact, the actual gas extraction equipment is not calibrated as a system. Therefore, what is needed is a way to calibrate a gas extraction system as a whole.

The subject matter of the present disclosure is directed to overcoming, or at least reducing the effects of, one or more of the problems set forth above.

SUMMARY OF THE DISCLOSURE

The present disclosure is directed to a way to calibrate a gas extraction system, such as a Constant Volume Trap (CVT) or a Heated Constant Volume Trap (HCVT), with techniques that can be implemented in the field.

In one embodiment, a method is used to calibrate efficiency of a gas extraction system in extracting hydrocarbons from mud flowing in a drilling operation. The method involves injecting, in at least one injection operation, at least one known concentration of at least one of the hydrocarbons into at least a portion of the mud flowing in the drilling operation and obtaining, with the gas extraction system during each injection operation, at least one subject reading of the at least one hydrocarbon extracted from the mud.

Relative to each injection operation, a determination with the gas extraction system can be, and preferably may be, made that a background reading of the at least one hydrocarbon extracted from the portion of the mud is at least indicative of stability. This determination can at least be made prior to the injection operation by obtaining a background reading and assessing it for stability. Further background readings could also be made. Without such stable background reading(s), the method may be terminated because a drilling event or the like may be occurring. For example, the method may be terminated should the background reading fail to reach a measurement level of stability, be inconsistent with other background readings, or evidence a type of drilling event. As an alternative, the method can instead divert some of the mud for containment and for later use in the injection and determination steps so as to avoid issues with inconsistent background readings.

In any event, a correction factor is determined for each of the at least one hydrocarbon for the gas extraction system by comparing each subject reading against its corresponding known concentration. In turn, operational readings of the at least one hydrocarbon extracted from the mud with the gas extraction system can then be corrected using the determined correction factor.

In the method, additional injection operations can be performed with additional known concentrations of the hydrocarbon(s) for refining the determination of the correction factors. In the method, for example, the steps of injecting and determining can involve obtaining, with the gas extraction system at least prior to a first injection operation, a first background reading of the at least one hydrocarbon extracted from the portion of the mud. In the first injection operation, a first known concentration of the at least one hydrocarbon is injected into the portion of the mud, and a first subject reading of the at least one hydrocarbon extracted from the mud is obtained with the gas extraction system during the first injection operation.

The first injection operation is stopped, and a second background reading of the at least one hydrocarbon extracted from the mud is obtained with the gas extraction system. As noted above, the background reading(s) can be checked for stability. In a second injection operation, a second known concentration of the at least one hydrocarbon is injected into the mud, and a second subject reading of the at least one hydrocarbon extracted from the mud is obtained with the gas extraction system during the second injection operation. In general, the second known concentration of the known fluid injected into the mud can be greater than, less than, or equal to the first known concentration.

Determining that a background reading is at least indicative of stability can involve one or more of: waiting for the background reading to reach a measurement level of stability; and determining that the background reading is consistent, to at least a threshold, in comparison to another of the background readings.

Injecting the known concentration of the at least one hydrocarbon into the mud can involve one or more of: bypassing a portion of a mud stream for injection and then recombining the bypassed portion with the remaining mud stream; and injecting a quantity of gas and/or liquid of the at least one hydrocarbon into the mud stream.

In the method, a mixture of the mud stream and the injected concentration can be pumped to a pressurized mixing volume. Then, a mixture of a diverted portion of the mud stream and the injected concentration can be subsequently mixed with a remaining portion of the mud stream from which it had been diverted.

To obtain the subject readings of the mud with the gas extraction system during the injection operation, a constant volume of the mud can be pumped to the gas extraction system, which can include a gas trap, and the pumped volume can be heated prior to the system (e.g., gas trap). Additionally, a gas sample from the gas extraction system can be analyzed with a gas chromatograph or other analyzer.

In the method, correcting the operational readings of the at least one hydrocarbon can further involve adjusting, based on the corrected operational readings, a parameter of the drilling operation, such as flow rate, pump rate, mud type, mud weight, surface back pressure, etc. and can involve managing a drilling event, such as a kick, an influx, a fluid loss, gas at surface, a high-pressure low-volume depletion, etc.

In another embodiment, a system is used to calibrate efficiency of gas extraction in extracting hydrocarbons from mud flowing in a drilling operation. The system comprises injection equipment, pump equipment, a volume, and mud flow control equipment. The injection equipment is in fluid communication with a stream of the mud flowing in the drilling operation and receives at least a portion of the stream of mud. The injection equipment is configured to inject at one or more times at least one known concentration of at least one hydrocarbon into the portion of the stream. The pump equipment is in fluid communication with injection equipment and pumps the portion of the stream with the injected concentrations at high pressure. The volume is in fluid communication with the pump equipment and mixes the portion of the stream with the injected concentration under a pressurized condition.

With respect to the mud flow control equipment, a mixer can mix the mixed portion of the stream with any remaining portion of the stream from which it may have been diverted before communicating the stream to the gas extraction system. A flow control in communication with the volume can control the flow of the mixed portion of the stream after mixing in the volume. Also, a flowmeter can be used to measure the flow of the stream of mud involved in the gas extraction process.

The known concentration of the at least one hydrocarbon can include a first concentration at a first time and an optional second concentration greater than, less than or equal to the first concentration at a second time. Moreover, the known concentration of the at least one hydrocarbon can include a gas concentration and/or a liquid concentration.

The system can further include a gas extraction system, such as a Constant Volume Trap (CVT), a Heated Constant Volume Trap (HCVT), a permeable gas membrane system, or other type of system for performing the gas extraction. The gas extraction system has a constant volume pump taking in the stream of the mud flowing in the drilling operation.

The system may further include a processing unit operatively coupled to memory, the injection equipment, the pump equipment, and the gas extraction system. The processing unit can be operable to determine correction factors of the gas extraction system in extracting hydrocarbons from the mud flowing in the drilling operation using the method steps outlined previously. Alternatively, the correction factors may be applied in a post processing mode.

The foregoing summary is not intended to summarize each potential embodiment or every aspect of the present disclosure.

DETAILED DESCRIPTION OF THE DISCLOSURE

Figure 1:
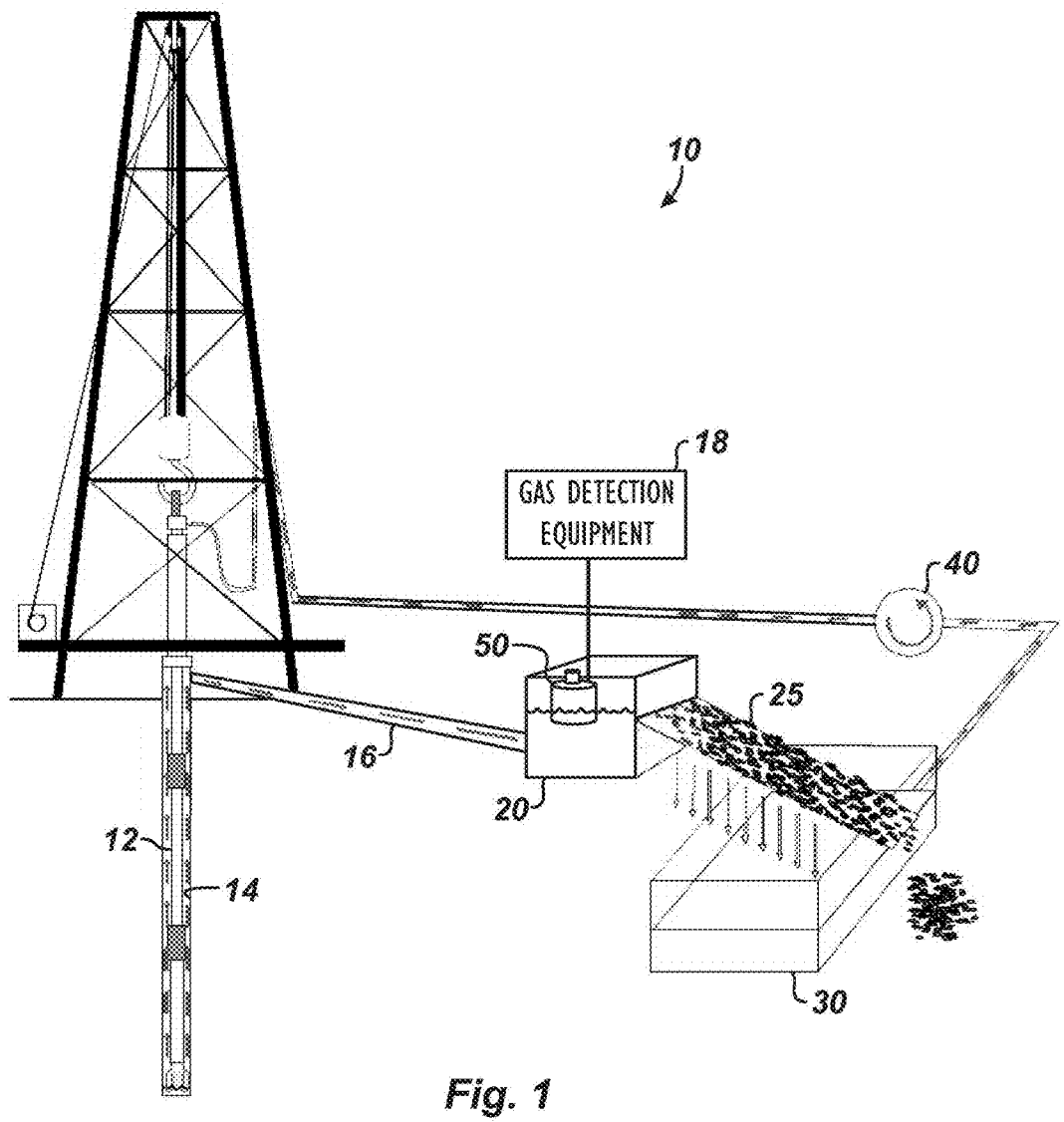
FIG. 1 illustrates a typical drilling rig as background to the present disclosure.
Figure 2:
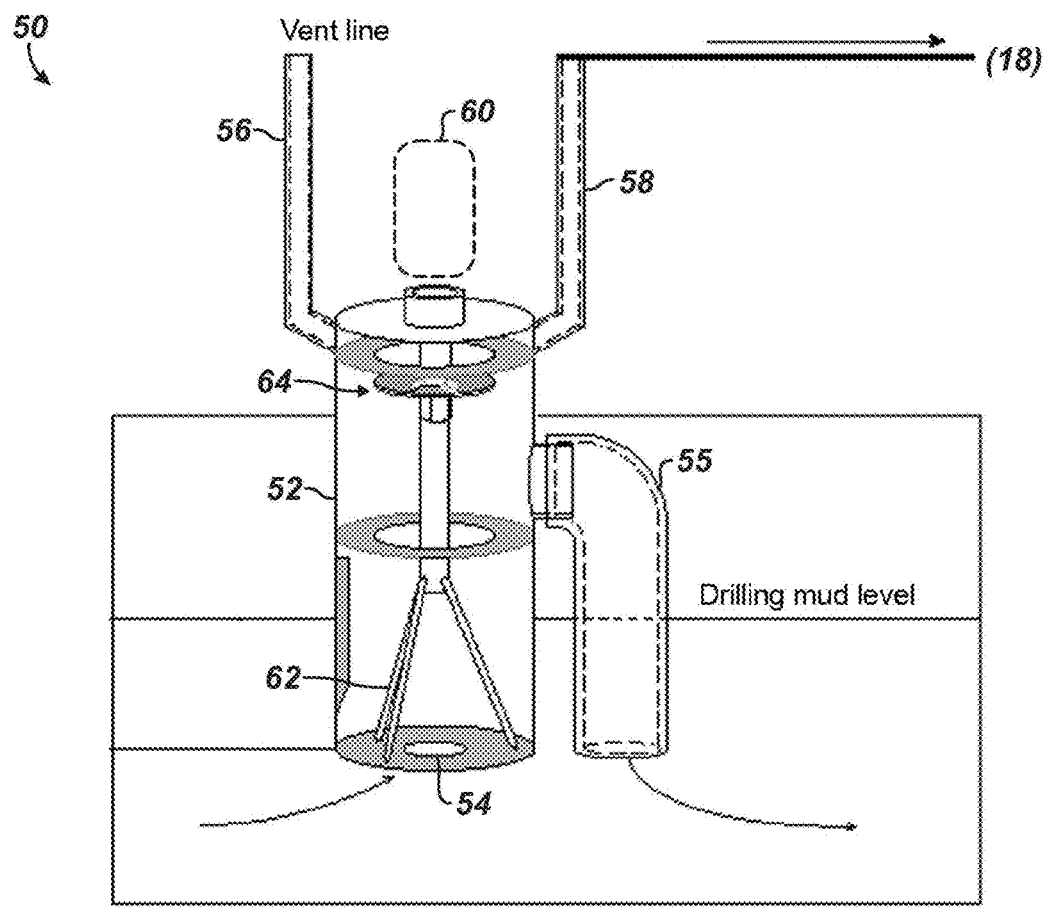
FIG. 2 illustrates a gas trap according to the prior art.
Figure 3A:
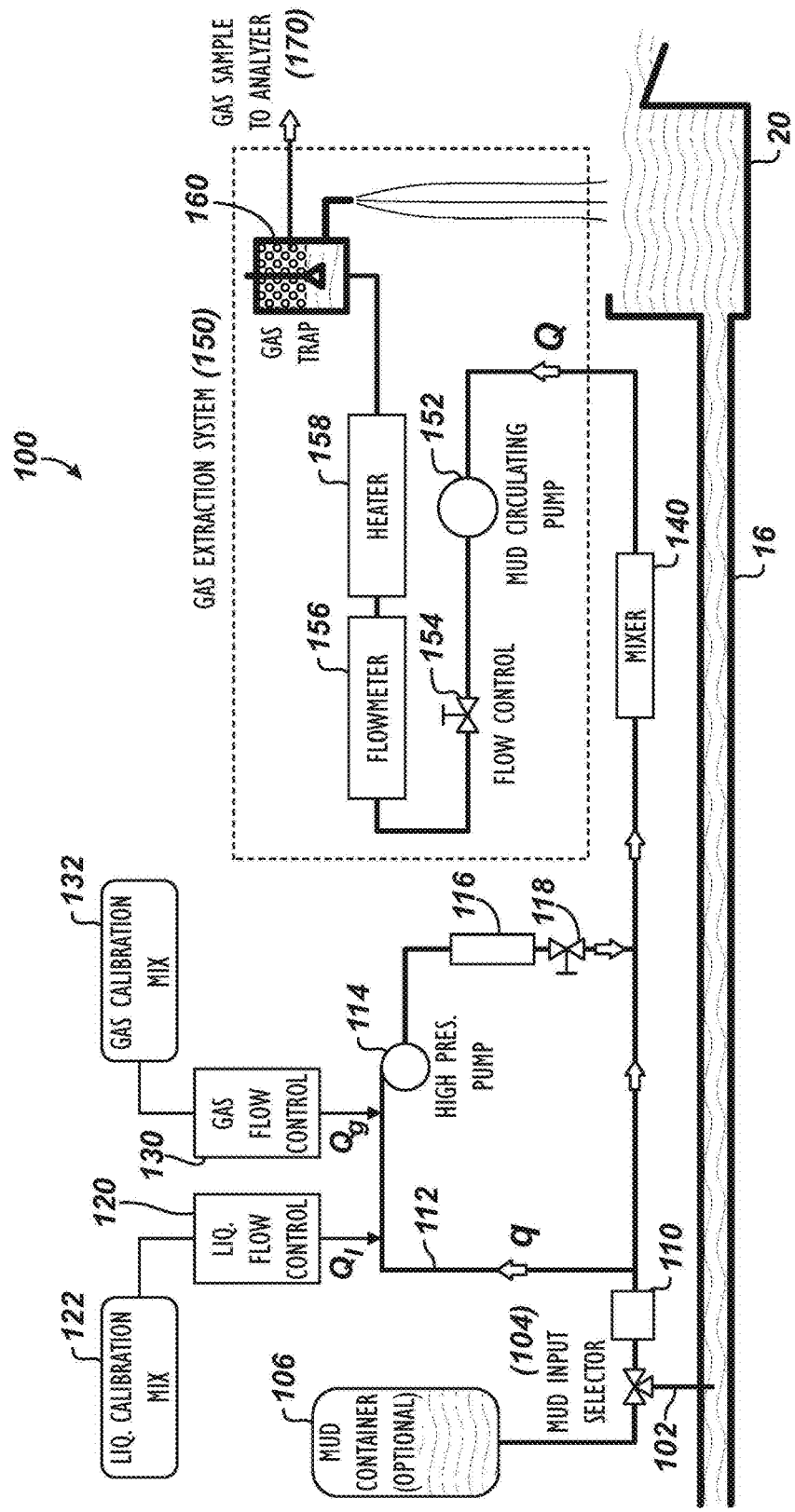
FIG. 3A illustrates a system according to the present disclosure.

FIG. 3A illustrates a system 100 according to the present disclosure. The system 100 includes various flow control and pump components or equipment (102, 104, 106, etc.), a flowmeter 110, injection components or equipment (120, 130, etc.), a mixer 140, and gas extraction equipment (i.e., a gas extraction system 150, a gas sample analyzer 170, etc.).

As shown, the system 100 can tap into the flow line 16 from the well (not shown) that leads to the possum belly 20 at the rig. This allows for a branched stream of the mud in the flow line 16 to be utilized. If practical, the system 100 can be more directly incorporated into the flow line 16.

A line 102 communicates with the mud stream in the flow line 16 and connects to one input of a mud input selector 104. Selection of the selector 104 can direct the mud stream from the flow line 16 or from an optional container 106 having mud. Either way, the mud stream is passed along a flow line 108 and may pass through a flowmeter 110, which can determine flow values for the various calibrations and determinations that follow.

A bypassed mud stream q sampled from the main flow passes along a flow line 112 to various injection components (120, 130, etc.) to inject a known quantity of fluid into the flow. For example, gas and/or liquids streams are injected in the bypassed mud stream q, sampled from the main mud stream. The combination may then mixed (emulsified) in a pressurized mixing volume 116 after a high pressure pump 114 has pumped the combination at high pressure. This mixing may be done without the need of pressurization. In this case, the pump 114 can be set instead as a circulating pump. Also, the $Q_l$ and $Q_g$ injections can be done directly into the mud stream in line 108, which would make the bypass loop 112 unnecessary.

For example, a liquid flow control 120 can inject a quantity $Q_l$ of a liquid calibration mix 122 into the mud stream in the flow line 112. Also, a gas flow control 130 can inject a quantity $Q_g$ of a gas calibration mix 132 into the mud stream in the flow line 112. The injected hydrocarbon concentration is produced to desired values by the liquid flow control 120 if the hydrocarbons are liquids (Ql) and/or by the gas flow control 130 if the hydrocarbons are gases (Qg). These controls 120 and 130 can include mass flow controllers, valves, solenoids, sensors, etc. Besides hydrocarbons, the gas injection stream Qg may have other gases of interest, such N2, He, $CO_2$, etc.

The high pressure pump 114 on the flow line 112 then pumps the mud stream with the injected fluid (liquid and/or gas) to the pressurized mixing volume 116, which can be a chamber or the like to mix the main flow and injected fluid under pressurized conditions. Finally, a flow control 118 can reintroduce the mixed volume mud back to the main stream in the flow line 108.

Then, the two mud streams are mixed together and sent to the gas extraction system 150 as a stream Q with a known concentration of hydrocarbons. For example, a mixer 140 along the flow line 108 ensures that the mixed volume mud and the main flow mud are mixed before the full flow Q enters the gas extraction system 150.

In the gas extraction system 150, the hydrocarbons are finally extracted and sent to the analytics to produce certain gas readings. These final gas readings are then related to the known amount of hydrocarbons injected and give extraction efficiency factors for the Gas Extraction System for that particular mud type.

As noted above, the gas extraction system 150 may be a Constant Volume Trap (CVT), a Heated Constant Volume Trap (HCVT), permeable gas membrane system, or other type of system. In the present embodiment, the gas extraction system 150 is a Heated Constant Volume Trap (HCVT) having an additional flow control 154 and flowmeter 156. As shown, the gas extraction system 150 includes a mud circulating pump 152 that feeds the mud stream to the optional flow control 154, the optional flowmeter 156, and a heater 158 before reaching a gas trap 160. The system 150 takes a predetermined stream Q using the constant volume pump 152. In this way, operation of the pump 152 samples a constant flow stream so that the various flowmeters 110, 156 may not be necessary but can provide redundancy.

The gas trap 160 finally extracts the hydrocarbons from the mud and sends a gas sample to the analytics to produce certain gas readings. For example, the gas trap 160 agitates the mud to extract the gas sample, which is then communicated to the gas sample analyzer 170, such as a gas chromatograph or other device. Mud from the gas trap 160 can be expelled to the possum belly 20. For the purposes of the present disclosure, features of the pump 152, heater 158, gas trap 160, analyzer 170, and the like can be typical devices.

During operation of the system 100, known concentrations of hydrocarbons are injected in the mud from the injection components 120, 130 by continuous injections of a predetermined hydrocarbon stream into the mud stream sampled by the mud circulating pump 152 of the gas extraction system 150. During operation, the injection equipment (120, 130) and other components can be bypassed when calibration is not in use. In these situations, the gas extraction system 150 can operate as normal to extract and analyze gas in the mud stream.

The disclosed system 100 can have various components for functioning and automation. For example, FIG. 3B briefly illustrates a schematic of some operational components for the disclosed system 100. As shown, the system 100 includes a control unit 210, which can include various types of processing units, hardware, software, and the like. The control unit 210 is operatively coupled to the analyzer 170, which provides the gas readings for the calibration of the system 100 as well as the standard gas readings from the gas extraction system 150 that are used in the normal course of drilling operations.

The control unit 210 is also operatively coupled to memory 212 storing various types of information, such as information on mud types, default variables for mud types, default parameterizations of hydrocarbon concentrations in different mud types, and determined correction factors for hydrocarbons in various mud types. In general, the parameterizations can include information on the solubility factor of the hydrocarbons in various mud types, and the parameterizations can be based on historical information, previous testing, etc. Additionally, the parameterizations can include information for extrapolating an extraction efficiency for one or more separate hydrocarbon components based on the relative extraction efficiency of at least one measured hydrocarbon component to the remaining others. In this way, analysis of the at least one measured correction factor for one hydrocarbon component can be used to extrapolate results for other components.

The control unit 210 is operatively coupled to any of a number of various sensors 214 for monitoring operation of the system and detecting parameters for analysis, such as flow, pressure, temperature, etc. Finally, the control unit 210 is operatively coupled to the flow controls 220, pump controls 230, and extraction controls 240 that monitor and operate the various components of the system 100. The unit 210 can interface with flow controls 220 including, for example, the liquid flow control (120), the gas flow control (130), the extraction's flow control (154), and the like of the system 100 discussed previously. The unit 210 can interface with the pump controls 230 including, for example, those for the high pressure pump (114), constant volume pump 152, and the like of the system 100 discussed previously.

The unit 210 can interface with the extraction controls 240 including, for example, those controls for detecting flow with the flowmeters 110, 156, for operating the gas trap 160, and the like of the system 100 discussed previously. Finally, the unit 210 can interface with drilling controls 250 used in the drilling operations. This can allow the information from gas extraction and analysis and the corrections made by the system 100 to be used in the control of drilling operations.

Figure 4:
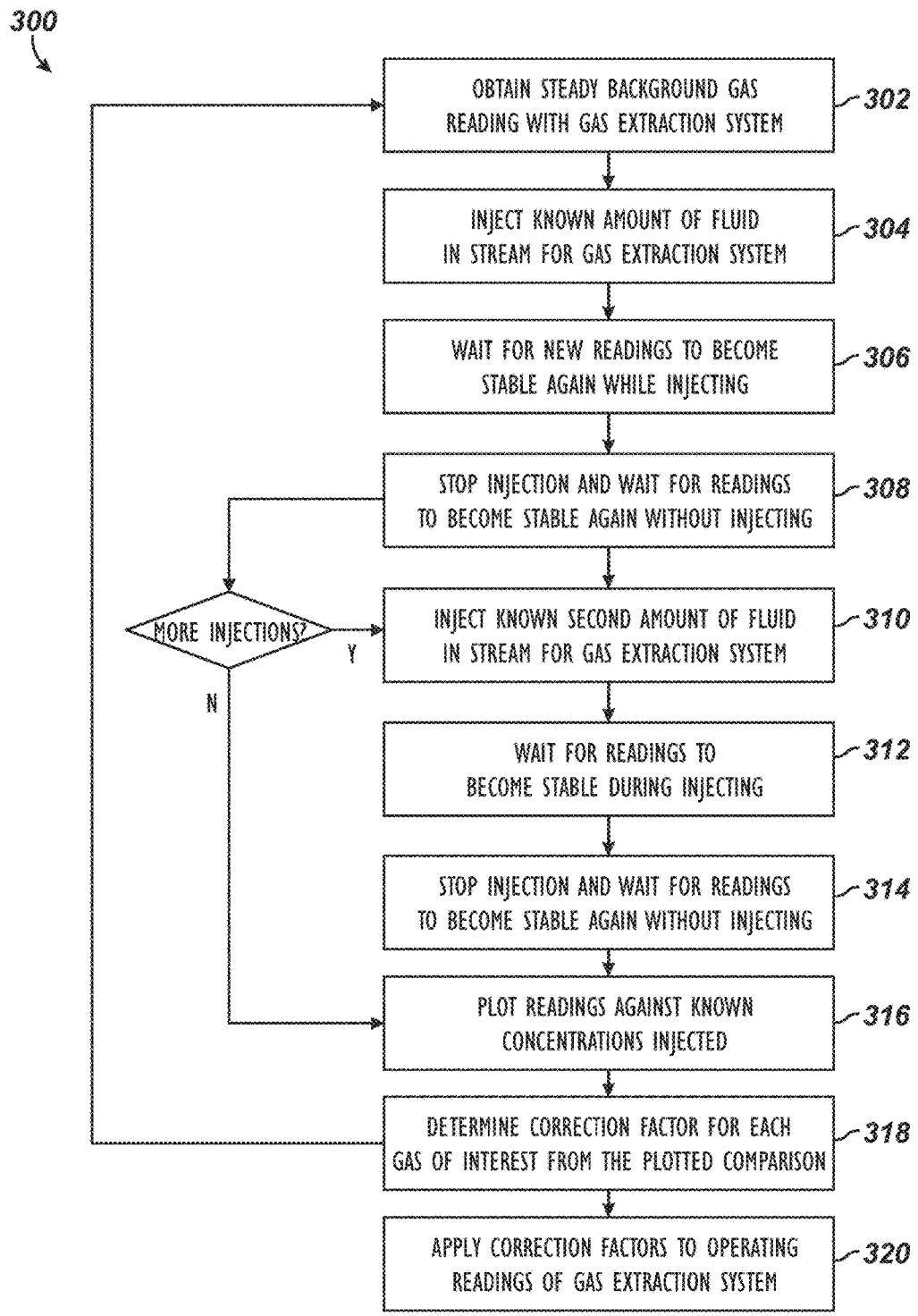
FIG. 4 illustrates a flowchart of a procedure to calibrate the gas extraction system of the present disclosure.

Having an overall understanding of the system 100 of the present disclosure, discussion turns to FIG. 4, which illustrates a procedure 300 of the present disclosure allowing the system 100 in the field to calibrate the gas extraction system 150 without the need to involve offsite resources.

In the procedure 300, the system 100 first runs the gas extraction system 150 as normal in the field and achieves a steady background gas reading (Block 302). Once readings are steady, they can be recorded for post-processing, or an advanced mode can record the readings in memory 212 for direct processing, the system 100 injects a known amount of fluid (e.g., gas and/or liquid) into the stream before the gas extraction system 150 via a T-port or the like (Block 304) and waits for the resulting readings to become stable again (Block 306). A first reading can be taken at a set time. In general, this first reading can be taken after the gas reading reaches a plateau and may consist of one or more readings averaged for the time length of the plateau.

The first injection readings can be recorded for post-processing, or an advanced mode can record the readings in memory 212 for direct processing. After recording the first injection readings (optionally in memory 212), the system 100 then turns off the injection and waits until the steady background gas readings return (Block 308). These second background readings are also recorded (optionally in memory 212.)

A single injection operation may be enough for the purposes of the system 100, especially if the procedure has already been performed. More than one second injections operation may alternatively be performed, which can provide better accuracy and can also be used as a consistency check to the previous injection(s). A decision for performing additional injections is schematically shown in FIG. 4. In actual processing, such decision may not necessarily take place because the procedure 300 may perform only one injection by default, in which case the procedure 300 would go directly to analysis steps discussed later.

For the purpose of the disclosure, discussion of the procedure 300 will now focus on at least a second injection operation being performed. It will be appreciated that various steps can be repeated any number of times to perform even more injections should they be desired.

Continuing with the procedure 300 in a second injection operation, the system 100 injects a second concentration of fluid into the stream (Block 310). This second concentration may be greater than, less than, or the same as the first concentration. Again, the system 100 waits for the resulting readings to become stable while injecting the fluid so that second injection readings can be taken at the set time (e.g., after a plateau is reached) in this repeated injection process (Block 312). After recording the second injection readings (optionally in memory 212), the system 100 then turns off the injection and waits until the steady background gas readings return (Block 314). These third background readings are also recorded (optionally in memory 212.)

All of the background and injection readings in Blocks 302-314 are being done while mud is flowing through the system 100. When the procedure 300 is performed in the field, for example, the mud coming from the well already contains a certain concentrations of hydrocarbons. To account for the concentrations in determining the extraction efficiency factors, the system 100 determines the background readings (Blocks 302, 308) prior to the injections (Blocks 304, 310). These background reading are taken on the mud itself so that the system 100 has a background for the existing gas content in the mud without the injections. Comparison of the background readings before and after the injection can indicate that a particular gas event (e.g., influx) is occurring while the mud is flowing, which could lead to incorrect results. In general, the background readings provide a factor for scaling the various results and are preferably consistent with one another during the procedure 300, indicating that an event is not occurring.

An alternative approach can eliminate variation in the mud's background concentrations. A certain mud volume can be sampled in prior steps of the procedure 300 and can be held in a mud container 106 of the system 100, as shown in FIG. 3. For the whole calibration period of the procedure 300, the mud used for the injections and analysis is supplied through the system 100 from this container 106 instead of from the flow line 16. In the system of FIG. 3, for example, this can be achieved by switching the mud input selector valve 104. This sampled mud would not be subject to variations from the ongoing drilling operation.

Continuing with the procedure 300, the system 100 performs final analysis of the readings. For example, the first injection readings from Blocks 304-306 (and additionally those of Blocks 310-312, if performed) are compared (e.g., plotted) against the pre-determined, known concentrations of the hydrocarbons that have been injected (Block 316). In the current procedure 300, at least one injection and at least one reading are necessary to provide the analysis. It is conceivable that more injection readings of different and redundant concentrations can be performed to further refine analysis, as also outlined above.

In the analysis, certain variables may need to be accounted for in the comparisons, including subject flow rates as well as what rate the hydrocarbons are being extracted. As briefly noted above, the analysis can also use default parameterizations of the hydrocarbons for the given mud type of interest. Such default parameterization may include information for the solubility factor of the hydrocarbons and may have been developed in research testing and calibration, which may be stored in lookup tables, formulas, algorithms, and the like in the memory 212 of the system 100.

For each gas (which may include, but is not limited to, C1 to C6), the plotted readings compared to the pre-determined, known concentrations of the hydrocarbon(s) that have been injected defines a correction factor, which may be calculated or which the system 100 determines (Block 318). As the line from Block 318 back to Block 302 indicate, the entire process 300 can be repeated as needed.

In general, the correction factor can be a constant or variable offset value or can be defined by a function, an algorithm, or other mathematical device, which may depend on the responses of the overall system 100 and the gas extraction system 150. Each correction factor for the gases of interest can thereby correct for gas extraction inefficiencies in the gas extraction system 150 under its current operating conditions. Accordingly, in the ongoing drilling operations, the gas extraction system 150 operates in its standard mode to obtain gas readings. The corrections might be applied either in a post-processing calculation, or the system 100 may apply the correction factors automatically to the operational readings obtained (Block 320). This can provide more accurate analysis of the gas content in the mud to better control the ongoing drilling operation.

For example, the drilling operation may seek to maintain a constant bottom hole pressure so that operating pressures need to be managed. The corrected operational readings of the hydrocarbons in the mud can therefore be use to adjust managed pressure parameters of the drilling operation, such as flowrate, pump rate, mud type, mud weight, surface back pressure, etc. and to manage events, such as kicks, influxes, fluid losses, gas at surface, high-pressure low-volume depletions, etc.

The procedure 200 can be repeated whenever anything changes in the mud properties. In this sense, the procedure 200 can operate as a continuous open stream calibration method to calibrate the system 100 while flowing mud through it. As noted previously, other solutions require the collection of mud and analysis of that mud whereas the current procedure 200 simply flows a pre-determined injection level through the mud and measures the extraction efficiency of the system 150 of that pre-determined level. Accordingly, the procedure 300 can be applied directly to real-time runs, and it does not necessarily require a prior mud sampling to be performed. This is especially true in cases when the mud gas background is steady (i.e., there are no drilling gas events).

By configuring the injection steps (i.e., Blocks 304, 310), what types and quantities of hydrocarbons are used, and the like, the procedure 300 can be used to simulate one or more quantified concentrations of hydrocarbons (and/or other gases) in the mud. This make it possible to get a multipoint response behavior of the gas extraction system 150 for a wide range of concentrations.

Finally, no hydrocarbons losses occur during the calibration in the procedure 300. Instead, the amount of hydrocarbons is a known variable as produced by the quantitative injections and are not an inferred variable after successive extraction runs, as in U.S. Pat. No. 7,392,138, do not require having PVT fluid analysis results, or do not rely on the microwave/steam still extraction efficiency, as may occur in U.S. Pat. No. 8,011,238. This system 100 calibrates the response for each specific mud type on each location and thus can produce a more consistent response with greater accuracy in predicting reservoir fluid type.

With respect to specific fluid properties such as hydrocarbon solubility, the system may employ a pre-determined relative extraction efficiency factor for each hydrocarbon based off of one hydrocarbon component. This method involves determining the correction factors by applying the above described procedure (300) for one hydrocarbon component. Then, for the rest of the components, the process calculates their correction factors based on the obtained correction factor and the relative extraction efficiency of the remaining components relative to the (original) one. This calculation can be done instead of (or in addition to) performing any injection operations related to the rest of the components. The relative extraction efficiency determination may be performed in separate analysis and processing.

Figure 3B:
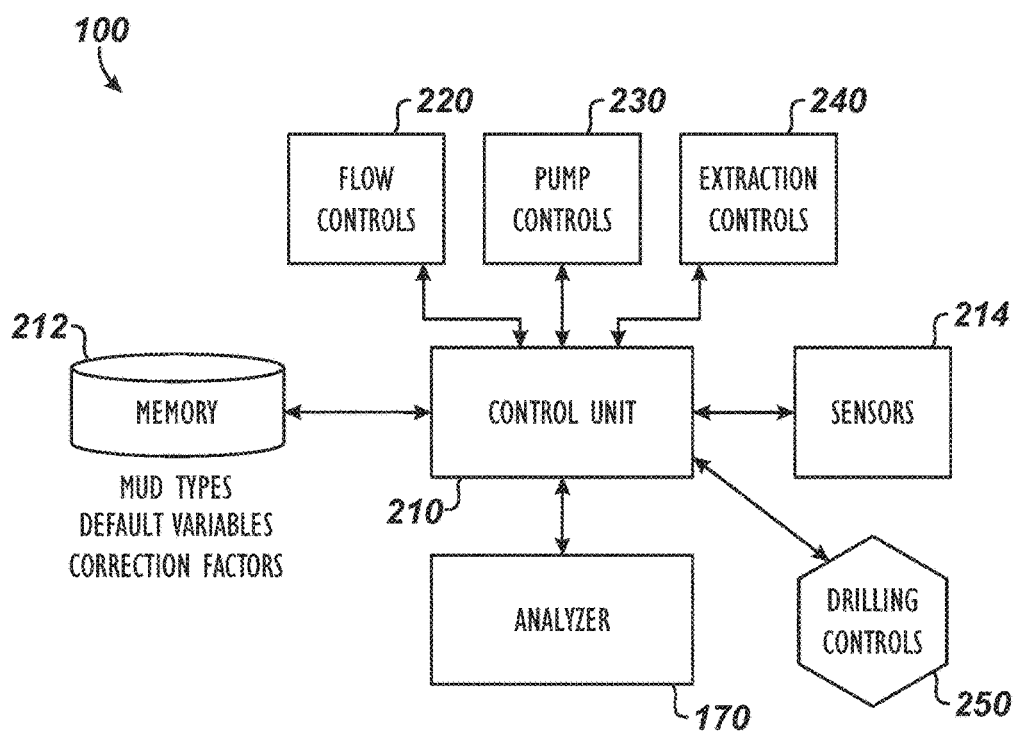
FIG. 3B illustrates an optional automation schematic of operational components for the disclosed system.

As will be appreciated, teachings of the present disclosure, such as related to the control unit 210 of FIG. 3B and the procedure 300 of FIG. 4 can be implemented in digital electronic circuitry, computer hardware, computer firmware, computer software, or any combination thereof. Teachings of the present disclosure can be implemented in a programmable storage device (computer program product tangibly embodied in a machine-readable storage device) for execution by a programmable control device or processor so that the programmable processor executing program instructions can perform functions of the present disclosure. The teachings of the present disclosure can be implemented advantageously in one or more computer programs that are executable on a programmable system including at least one programmable processor coupled to receive data and instructions from, and to transmit data and instructions to, a data storage system, at least one input device, and at least one output device. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter.

In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A method to operate a gas extraction system in extracting at least one hydrocarbon from mud flowing in a drilling operation, the method comprising:
   directing at least a portion of the mud flowing in the drilling operation to the gas extraction system;
   injecting, in at least one injection operation, at least one known concentration of the at least one hydrocarbon into the directed mud and obtaining, with the gas extraction system during each injection operation, at least one subject reading of the at least one hydrocarbon extracted from the directed mud;

determining a correction factor of each of the at least one hydrocarbon for the gas extraction system by comparing each subject reading against its corresponding known concentration;

obtaining, with the gas extraction system, at least one operational reading for the at least one hydrocarbon extracted from the directed mud; and correcting the at least one operational reading using the determined correction factor.

2. The method of claim 1, wherein injecting the at least one known concentration of the at least one hydrocarbon into the directed mud comprises pumping a mixture of the directed mud and the injected concentration to a pressurized mixing volume.

3. The method of claim 1, wherein obtaining, with the gas extraction system during the at least one injection operation, the subject reading of the directed mud comprises pumping a constant volume of the directed mud to the gas extraction system.

4. The method of claim 1, wherein determining the correction factor of each of the at least one hydrocarbon for the gas extraction system comprises:

determining a first of the correction factor for a first component of the at least one hydrocarbon according to the steps of claim 1; and calculating, from the first correction factor for the first component, one or more second of the correction factors for one or more second components of the at least one hydrocarbon.

5. The method of claim 1, wherein injecting the at least one known concentration of the at least one hydrocarbon into the directed mud comprises:

bypassing a portion of a mud stream from the directed mud for injection;

injecting a quantity of gas and/or liquid of the at least one hydrocarbon into the bypassed mud stream; and recombining the bypassed portion with a remaining portion of the mud stream.

6. The method of claim 5, wherein recombining the bypassed portion with the remaining portion comprises mixing a mixture of the bypassed portion of the mud having the injected concentration with the remaining portion of the mud stream.

7. The method of claim 1, further comprising adjusting, based on the corrected operational reading, a parameter of the drilling operation, wherein the parameter is selected from the group consisting of a flow rate, a pump rate, a mud type, a mud weight, and a surface back pressure.

8. The method of claim 7, further comprising managing a drilling event based on the adjusted parameter, wherein the drilling event is selected from the group consisting of a kick, an influx, a fluid loss, gas at surface, and a high-pressure low-volume depletion.

9. The method of claim 1, further comprising diverting some of the directed mud for containment and for later use in the injection and determination steps.

10. The method of claim 9, wherein diverting some of the directed mud for containment and for later use in the injection and determination steps comprises operating a selector selectively communicating between the containment, the gas extraction system, and a flow line of the mud flowing in the drilling operation.

11. The method of claim 1, further comprising determining, with the gas extraction system relative to the at least one injection operation, that a background reading of the at least one hydrocarbon extracted from the directed mud is at least indicative of stability.

12. The method of claim 11, wherein determining that the background reading is at least indicative of stability comprises one or more of:

waiting for the background reading to reach a measurement level of stability; and determining that the background reading is consistent in comparison to another relative background reading.

13. The method of claim 11, comprising terminating the method in response to a determination that the background reading of the at least one hydrocarbon extracted from the directed mud is indicative of instability, wherein the determination indicative of instability comprises a determination that the background reading fails to reach a measurement level of stability, is inconsistent with other background readings, or evidences a drilling event.

14. The method of claim 1, wherein injecting the at least one known concentration of the at least one hydrocarbon into the directed mud comprises:

injecting the at least one known concentration with injection equipment, the injection equipment in fluid communication with the directed mud and receiving at least a portion of the directed mud, the injection equipment configured to inject the at least one known concentration of the at least one of the hydrocarbons into the directed mud;

pumping, with pump equipment in fluid communication with the injection equipment, the directed mud with the injected concentration at high pressure; and mixing, in a volume in fluid communication with the pump equipment, the directed mud with the injected concentration under a pressurized condition prior to the gas extraction of obtaining the at least one subject reading with the gas extraction system.

15. The method of claim 14, wherein mixing further comprises mixing, with a mixer, the mixed portion of the directed mud with any remaining portion of the directed mud before communicating the directed mud for the gas extraction.

16. The method of claim 14, wherein mixing further comprises controlling, with a flow control in communication with the volume, flow of the mixed portion of the directed mud after mixing in the volume.

17. The method of claim 14, wherein obtaining, with the gas extraction system during the at least one injection operation, the at least one subject reading of the at least one hydrocarbon extracted from the directed mud comprises performing the gas extraction with the gas extraction system in fluid communication with the volume, wherein the gas extraction system comprises a constant volume pump taking in a stream of the directed mud.

18. The method of claim 14, wherein obtaining the at least one subject reading and determining the correction factor comprises using a processing unit operatively coupled to the injection equipment and the pump equipment, the processing unit being operable to obtain the at least one subject reading from the gas extraction and to determine the correction factor of the gas extraction in extracting the at least one hydrocarbon from the directed mud.

19. The method of claim 1, further comprising performing additional injection operations and determinations; and refining the determined correction factor of each of the at least one hydrocarbon based thereon.

20. The method of claim 19, wherein the steps of injecting and determining in the additional injection operations and determinations performed comprise:

obtaining, with the gas extraction system at least prior to a first of the at least one injection operation, a first background reading of the at least one hydrocarbon extracted from the directed mud;

injecting, in the first injection operation, a first of the known concentration of the at least one hydrocarbon into the directed mud and obtaining, with the gas extraction system during the first injection operation, a first of the at least one subject reading of the at least one hydrocarbon extracted from the directed mud;

stopping the first injection operation and obtaining, with the gas extraction system, a second background reading of the at least one hydrocarbon extracted from the directed mud; and injecting, in a second of the at least one injection operation, a second of the known concentration of the at least one hydrocarbon into the directed mud and obtaining, with the gas extraction system during the second injection operation, a second of the at least one subject reading of the at least one hydrocarbon extracted from the directed mud.

21. The method of claim 20, wherein the second known concentration is greater than, less than, or equal to the first known concentration.

* * * * *